United States Patent
Suzuki

(10) Patent No.: US 6,527,967 B1
(45) Date of Patent: Mar. 4, 2003

(54) THIN PIECE FORMING METHOD

(75) Inventor: Hidekazu Suzuki, Chiba (JP)

(73) Assignee: Seiko Instruments, Inc., Chiba (JP)

(*) Notice: Subject to any disclaimer, the term of this patent is extended or adjusted under 35 U.S.C. 154(b) by 0 days.

(21) Appl. No.: 09/356,234

(22) Filed: Jul. 16, 1999

(30) Foreign Application Priority Data

Jul. 16, 1998 (JP) .......................................... 10-202298

(51) Int. Cl.[7] .............................................. B44C 1/22
(52) U.S. Cl. ........................ 216/62; 216/65; 216/66; 438/712; 438/940; 438/977
(58) Field of Search ..................... 216/62, 65, 66; 438/712, 940, 977; 430/323; 204/192.34, 298.36

(56) References Cited

U.S. PATENT DOCUMENTS

| | | | | |
|---|---|---|---|---|
| 5,009,743 A | * | 4/1991 | Swann | 156/643 |
| 5,440,123 A | * | 8/1995 | Ikeda | 250/307 |
| 5,472,566 A | * | 12/1995 | Swan et al. | 156/643.1 |
| 5,922,179 A | * | 7/1999 | Mitro et al. | 204/298.04 |

FOREIGN PATENT DOCUMENTS

| | | | | |
|---|---|---|---|---|
| DE | 4112375 A1 | * | 4/1991 | ............ G01N/1/28 |
| JP | A-05-231998 | | 2/1992 | |
| JP | A-04-76437 | | 3/1992 | |
| JP | A-06-134583 | | 5/1994 | |
| JP | A-06-190569 | | 7/1994 | |
| JP | 8-5528 | | 1/1996 | |
| JP | 8-7121 | | 1/1996 | |
| JP | A-09-306411 | | 11/1997 | |

* cited by examiner

Primary Examiner—Frankie L. Stinson
(74) Attorney, Agent, or Firm—Pillsbury Winthrop LLP

(57) ABSTRACT

A method of forming a thin-piece sample for use in an electron microscope. The ion beam scanning used for etching a sample block to form a thin-wall portion is initiated from the outer perimeter of two opposite sides of the sample block to be formed, one side at a time, and the ion beam is directed from the outer perimeter of the sample block inwards towards the center of the sample block. When the two sides of the sample block are etched from the outside into the sample block, a thin wall is produced at the interior portion of the sample block. Also, a plurality of samples may be set in a known positional relationship, and a series of forming functions, including ion beam scanning, may be programmed for automation, allowing a plurality of samples to be formed all at one time easily and efficiently.

6 Claims, 4 Drawing Sheets

THIN PIECE FORMING METHOD

BACKGROUND OF THE INVENTION

The present invention relates to a method of efficiently forming thin-piece samples for use in a transmission electron microscope (TEM), or the like, using a focused ion beam (FIB).

Section TEM samples are required to be formed so that the desired point of observation is at a thickness through which an electron beam can be transmitted. Conventionally, it has been well known that an ion beam may be used to form a test/examination sample into a desired shape. Forming a sample for use in a transmission electron microscope (TEM) is performed by cutting the sample, using a focused ion beam, to a proper thickness so that electrons can transmit through the sample. This sample forming method is disclosed in the reference entitled, "Section TEM Sample Forming Method Using a Focused Ion Beam", 37th Applied Physical Academy, March 1990. Also, Japanese Patent Application No. 192641/1990 (JP-A-4-76437), filed by the present applicant, is also related to this technology. When a sample is machine-polished down to approximately several 10 $\mu$m, it is further cut at opposite surfaces of an observational point by ion beam etching so as to leave a thin wall of less than 1 $\mu$m, which makes it more convenient to confirm and observe a forming position, forming shape, section, etc. The prior application discloses an invention where a scanning electron microscope irradiating an electron beam is arranged so as to form a sample while monitoring a forming portion of the sample. Furthermore, disclosure is also made of the technology where the sample surface is locally formed with a film so as to prevent any damage due to the ion beam, and the inclination angle of a forming surface resulting from a convergent angle of the ion beam is compensated for by using an inclination setting in a table holding the sample in order to produce evenness in the sample thickness.

A summary of the basic technology of a focused ion beam forming apparatus for the present invention will be explained referring to an embodiment of the prior application shown in FIG. 5.

When a sample 4 to be formed is placed on a stage 5, the sample chamber is placed in a vacuum state by a vacuum apparatus (not shown), The sample stage 5 is set to a desired positional angle by a drive mechanism (not shown). The drive mechanism, in general, is capable of: (1) displacement in the X, Y and Z directions, (2) ion beam axis rotation, and (3) adjustment in angle relative to an ion beam axis. When a forming region is determined, a region of the sample having an end portion of a thin wall is exposed to a chemical vapor deposition (CVD) gas from the gas gun 9 in order to prevent damage to the portion by the ion beam, and a metal protection film is formed. Next, the forming region is irradiated by an ion beam and cut by sputtering. In this case, the relative displacement of the ion beam 2 and the sample 4 is made by scanning the ion beam with the deflection member of the electrostatic optical system 3, without using a drive device, because the forming requires extreme precision on the order of microns. Initially, the ion beam current is adjusted to increase the sputter rate in order to shorten the process time, thereby performing rough forming. Finally, the ion current is decreased in the area of the sample forming region, thereby performing precision forming. The feature of this apparatus lies in a structure where an electron beam can be irradiated to a sample for sample surface observation in a direction different than that of the ion beam. Because of this arrangement, an electron beam 7 may be solely used for scanning a sample that would have been damaged by an ion beam. The secondary charged particles (electrons) 11 are then detected by the secondary charged particle detector 10. Thus, observations may be made at the same time the samples are formed without taking the samples out of the apparatus. Also, because scanning electron microscope (SEM) images and scanning ion microscope (SIM) images are different due to the different kinds of secondary charged particles 11 emitted from the sample, images having different resolutions may be obtained. Accordingly, both images can be compared side-by-side on a display 13.

FIGS. 2A to 2D refer to the forming of a sample for use in a transmission electron microscope (TEM). A holding piece (not shown) is fixed with a sample block 4 that is mechanically cut out and is placed on a sample table (stage) 5 of the focused ion beam apparatus through a holder (not shown), and an ion beam 2 is irradiated to form the sample (see also FIG. 5). The specific procedure is as follows. In the first step, as shown in FIG. 2A, a sample 4 is a sectionally convex-formed block formed by mechanical cutting, and the sample is placed on the sample stage 5 (see FIG. 5). Next, a forming frame of the sample is determined, and, in order to prevent damage by the irradiating ion beam to the end portion being formed into a thin wall, a CVD gas (e.g., phenanthrene $C_{14}H_{10}$) is applied to that portion, thereby forming a protective coating layer 41 (as shown in FIG. 2B). In the next step, an ion beam 2 is irradiated and the sample block is cut at opposite surfaces by sputtering. Thus, a thin wall 42 of a sample becomes formed as shown in FIG. 2C. This sample for use in a transmission electron microscope has no differences in the shape of the opposite surfaces, and the sample is required to be of a thickness where an incoming electron beam 7 to the thin wall from a perpendicular direction can transmit through the thin wall (being 0.5 $\mu$m or less), as shown in FIG. 2D.

When reducing the thickness of a sample by using an ion beam, the material at the opposite surfaces of a predetermined region on the sample block is sputtered out, thereby making a desired thin wall 42 (as shown in FIG. 2C). The ion beam is scanned in a raster-like fashion to gradually cut the wall surface. As shown in FIG. 1A, the main scanning is made in a wall width direction (X direction), while sub-scanning is made in a wall thickness direction (Y direction). The directions of the main scanning and sub-scanning are generally built into the ion beam forming apparatus, and the formation of the thin wall on one side of the sample block is first performed by cutting along the surface from an outer wall and gradually advancing deeper into the sample block. On the other side of the sample block, an ion beam is irradiated into a predetermined position in the interior of the sample block, and the sample block on the other side is cut inside-out from the sample block. That is, the hole width is gradually increased in an outer-wall direction, and finally the outer wall is cut out in process.

As shown in FIG. 3, the cutting speed for a silicon substrate sputtering with an ion beam has specific incident angle characteristics. More specifically, a value of 0 is given for a cutting speed at a beam incident angle of 90 degrees to the surface to be formed, because the beam cannot be irradiated onto the sample surface. However, as the ion beam is inclined a little to enable irradiation to the sample surface, the cutting speed abruptly increases to peak out at about 80 degrees. As the angle of the ion beam is adjusted, the forming efficiency gradually decreases to the value at 0 degrees, which is an angle of an incident beam in the perpendicular direction to the surface to be formed, wherein the characteristic in cutting speed is about ⅛ that of the peak value. The positional relationship between the sample and the ion beam to be irradiated, as can be understood from FIG. 2C and FIGS. 4A and 4B, is maximized for the greatest efficiency at an incident angle of approximately 80 degrees. However, when forming a hole in parallel with the inner end wall surface (that is, cutting the sample block from the inside-out), the forming is naturally started at a lower efficiency rating because the incident ion beam angle is initially at 0 degrees (that is, the beam is directly perpendicular to the sample surface). When cutting the sample block from the outer wall inwards, the sample material that is cut out by sputtering is scattered to the outside of the sample block and away from the interior of the sample block. However, when the sample block is cut from the inside-out by cutting a hole parallel with the inner end wall surface, the sample material that is sputtered remains inside the hole, some of which re-adheres (see FIG. 4B, 44) to the bottom or adjacent wall surface of the sample block being cut. Therefore, when the sample block is cut from the inside-out, multiple passes with the ion beam must be performed in order to properly cut out the sample block. Although the time required to make multiple-passes with the ion beam is not a significant obstacle when only forming one sample a day, it does become a problem when 5 to 6 samples are required to be formed in a single day.

SUMMARY OF THE INVENTION

The present invention is directed to a method of forming a thin-piece sample for use in an electron microscope. The ion beam scanning used for etching a sample block to form a thin-wall portion is initiated from the outer perimeter of two opposite sides of the sample block to be formed, one side at a time, and the ion beam is directed from the outer perimeter of the sample block inwards towards the center of the sample block. When the two sides of the sample block are etched from the outside into the sample block, a thin wall is produced at the interior portion of the sample block.

Also, a plurality of samples may be set in a known positional relationship, and a series of forming functions, including ion beam scanning, may be programmed for automation, allowing a plurality of samples to be formed all at one time easily and efficiently.

DETAILED DESCRIPTION OF THE INVENTION

Figure 2A:
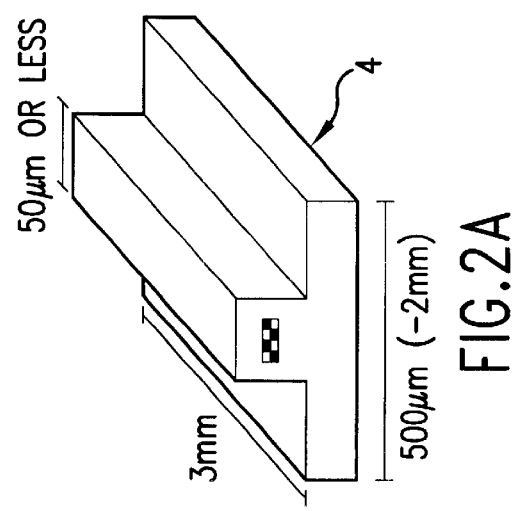
FIG. 2A is a perspective view of a sample block formed by mechanical cutting.
Figure 2B:
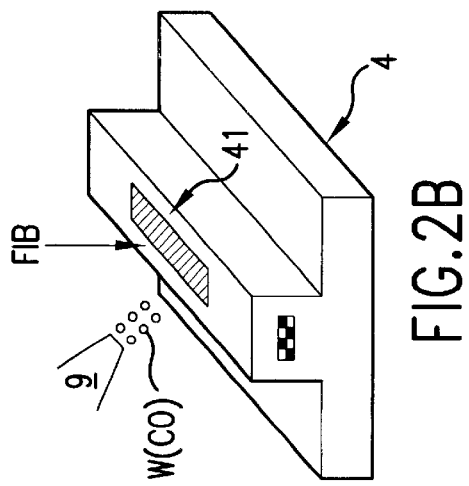
FIG. 2B is a perspective view showing a metal protection film formed at the thin-wall end portion using a gas gun and then irradiated by an ion beam.
Figure 2C:
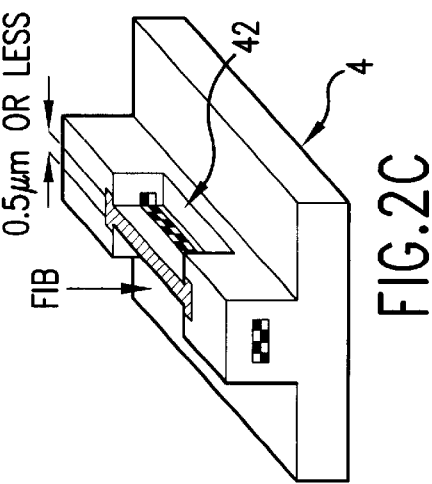
FIG. 2C is a perspective view of a sample formed into a thin piece by an ion beam.
Figure 2D:
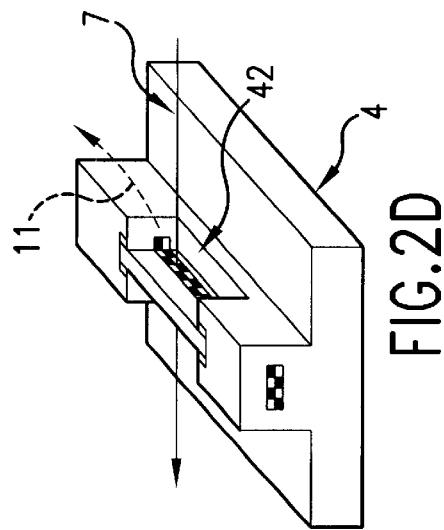
FIG. 2D is a perspective view showing a positional relationship between a created TEM sample and a transmission electron beam.
Figure 3:
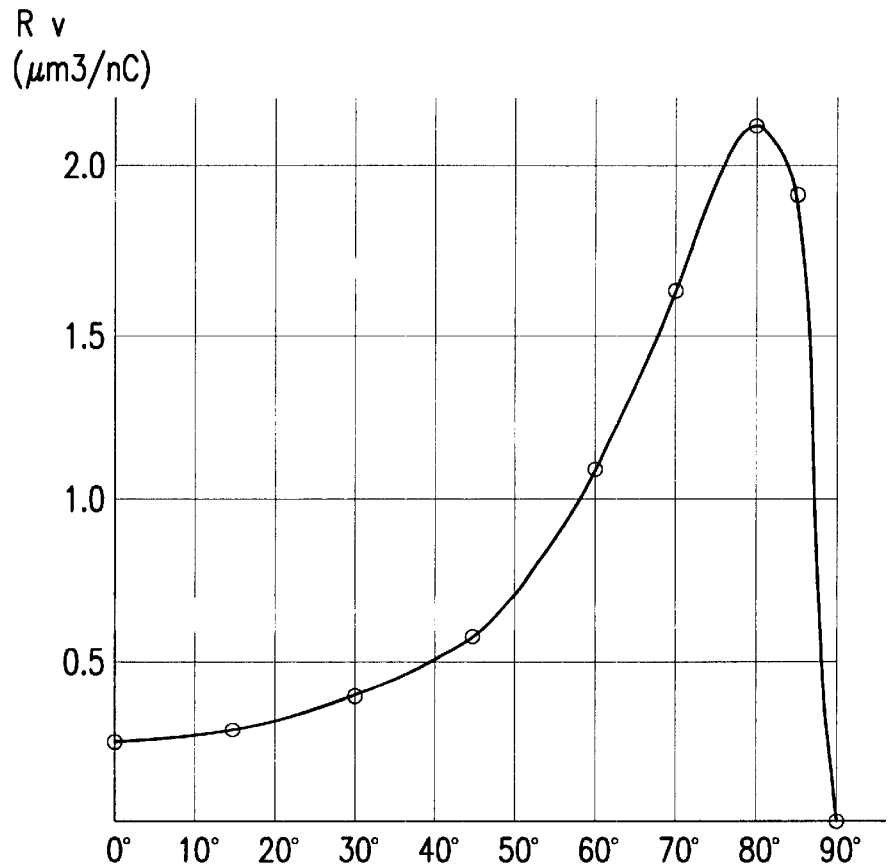
FIG. 3 illustrates a graph showing a relationship between an etch rate and an incident angle of the ion beam.

The thin piece forming of a transmission electron microscope sample by an ion beam requires that there are no differences in the shape of the opposite surfaces, and that the sample is preferably formed to a thickness where an electron beam 7 emitted in a perpendicular direction to the thin wall 42 can transmit through the thin wall (being 0.5 $\mu$m or less), as shown in FIG. 2D. In forming this thin wall, and in order to prevent damage to the thin wall end portion due to ion beam irradiation, a chemical vapor deposition (CVD) gas is applied from a gas gun 9 (as shown in FIG. 2B). At the same time, an ion beam is irradiated to form a protective coating layer 41. Thereafter, a thin wall surface can be formed as shown in FIG. 2C. In the first stage of the forming process, the beam current is increased in order to carry out a rough cut of the sample block in order to save time. If the beam current is increased, the etch rate is increased, but the formed surface finish becomes rough, which is useless as a TEM sample. Accordingly, in a final stage of the forming process, the beam current is decreased in order to carry out fine forming to finish the sample surface.

Figure 1B:
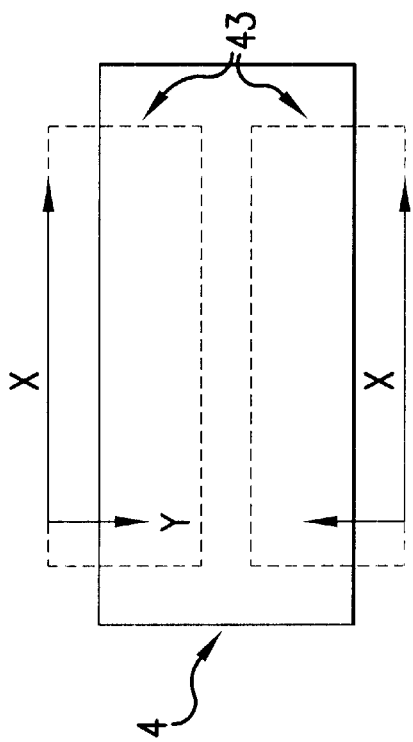
FIG. 1B is a top view from an ion beam source of beam scanning directions according to an embodiment of the present invention.
Figure 1A:
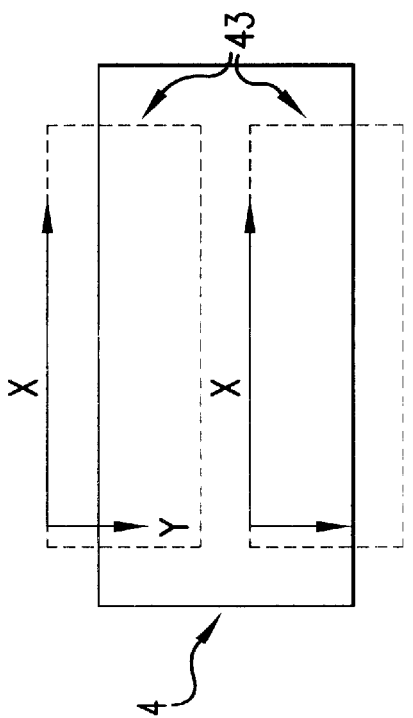
FIG. 1A is a top view from an ion beam source of conventional beam scanning directions relative to a sample.

The present invention is to alter the beam scanning direction from the conventional methods during "rough cutting", thus implementing a more efficient method. Referring to FIGS. 1A and 1B, the solid line portion is a sample block 4, and the broken line portion shows a forming area to be etched by an ion beam. Also, the X-direction arrow shows a direction of the main scanning, and the Y-direction arrow shows a sub-scanning direction. As understood from FIG. 4A (depicted by an exaggeration in angle for instructional purposes only), the ion beam, despite being a beam, is not perfectly linear, but possesses a convergence angle ($\alpha$) of several degrees, so that the sample surface to be formed does not become parallel with the ion beam axis, but rather has an angular difference of about $\alpha/2$. Accordingly, beam irradiation is conducted by inclining a sample stage 5 by the corresponding amount during the forming process.

Figure 4A:
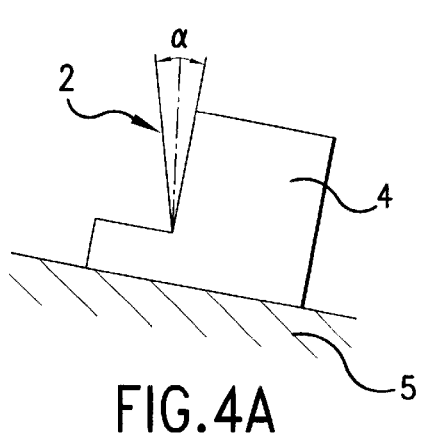
FIG. 4A is a side view showing a focused ion beam forming of the sample block from an outer wall surface side of the sample block.
Figure 4B:
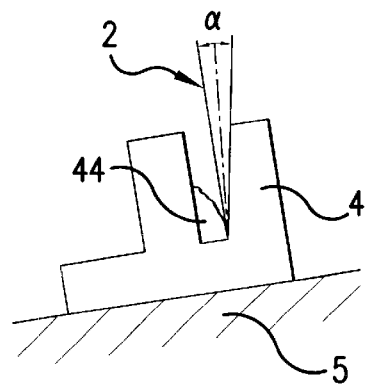
FIG. 4B is a view showing a focused ion beam forming of the sample block from the inside-out of the sample block.
Figure 5:
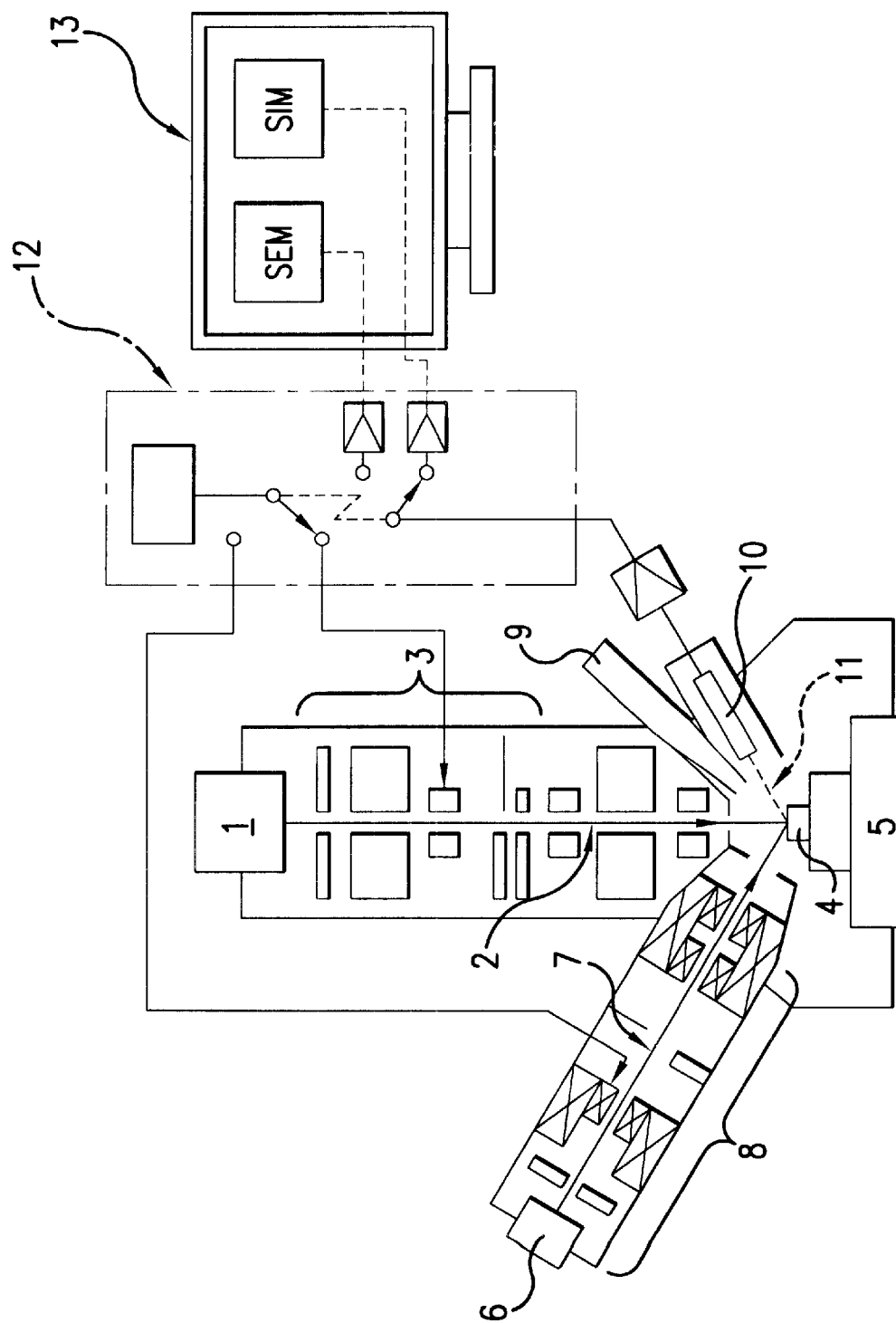
FIG. 5 is a schematic view showing an example of an ion beam forming apparatus.

As shown in FIG. 1B, ion beam forming according to an embodiment of the present invention is conducted on the sample by performing, on one side of the sample block, main scanning in an X-direction (from left to right on the figure) and sub-scanning in a Y direction (from top to bottom in the figure), as in the conventional method. In the case of this ion beam scanning, as shown in FIG. 4A, irradiation is made at a low angle with respect to the outer wall surface of the sample, at an incident angle of nearly 90 degrees. Accordingly, a high etch rate is made and the sputtered-out sample material is scattered towards the outside of the sample block, enabling an efficient forming process. Once the forming on this side of the sample block is completed, the other side of the sample block is formed to produce the thin wall. In an embodiment of the present invention, as shown in FIG. 1B, the X-direction main scanning is performed as in the conventional method (that is, from left to right). However, when the Y-direction sub-scanning is made here, it is performed differently than in the conventional method. The Y-direction sub-scanning of an embodiment of the present invention in forming the other side of the sample block, is performed in a reverse direction than that of the conventional method (i.e., the beam scanning is made in a direction from bottom to top, as in FIG. 1B). More specifically, the beam scanning is made from the outside of the sample block inwards (outside-in) rather than in the convention method, which is inside-out. The beam scanning is controlled and driven by a deflection device, which is part of an electrostatic optical system 3 of the ion beam forming apparatus. Although this special scanning method may be manually performed by a switch member, it is more convenient to store a forming sequence program in a memory device of a control device (not shown). With this beam scanning method, the thin wall on the other side of the sample block is formed from the outer wall surface side instead of forming from the interior of the sample block. Consequently, there is no necessity to start the forming process from a low incident angle of 0 degrees, which has a low etch speed. Therefore, it becomes possible to always form a sample using an angle with a high corresponding etch rate. Also, the sample materials that are cut and scattered by the sputtering and that re-adheres to the bottom and nearby wall portions, as shown at 44 in FIG. 4B in the prior method, are eliminated here. Accordingly, it is no longer necessary to perform multiple passes with the ion beam to remove the sample materials that have re-adhered to the bottom and nearby wall portions of the sample block, thus creating a more efficient forming process.

The forming process time for a TEM sample having 15 $\mu$m×15 $\mu$m×10 $\mu$m (width, height and depth) required 27 minutes in the conventional method, but employing the method according to an embodiment of the present invention, the forming process is completed in about 14 minutes. Generally, the improved method is about two to three times faster than the conventional method.

In order to further save time, a plurality of samples may be set on a holder placed on a sample stage and held in a known positional relationship to the ion beam, instead of setting and forming one sample at a time. By forming a plurality of samples at the same time, the preparation process for preparing the samples to the formed need not be repeated for each sample to be formed (such as setting a sample in the apparatus, vacuum evacuation within a sample chamber, setting the positioning angle of the sample relative to an ion beam, setting the drive-control for ion beam scanning for one side forming, setting the positioning angle for the other side forming, using a different ion beam scanning drive control for forming, and positioning the next sample to be formed). It is also convenient to store, as a program, a forming process sequence for automatically performing most of the functions to form a sample in a memory device of the control device. This initial forming process is not the "finish forming" for the TEM sample, but the "rough forming" process. Once this initial forming process is automated, it is no longer necessary to require a person to be in attendance of the apparatus. It is even possible to perform the automated "rough forming" in an unattended state during night time. Therefore, a plurality of samples may be automatically formed, leading to a drastic reduction in the time required for sample forming.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein.

What is claimed is:

1. A method of forming a thin-piece sample for use in a transmission electron microscope, comprising:

irradiating a single focused ion beam in a raster pattern from above an upper surface of a raw sample starting from a point on a first outer edge of the upper surface across the first outer edge to a second point on the first outer edge in a main scanning direction, being a wall-width direction, to remove a first planar section of the raw sample, and successively irradiating the single focused ion beam in the main scanning direction inwards toward a center of the raw sample in a first sub-scanning direction, being a wall-thickness direction, to remove planar sections successive to the first planar section of the raw sample; and irradiating the single focused ion beam in the raster pattern from above the upper surface of the raw sample starting from a point on a second outer edge of the upper surface across the second outer edge to a second point on the second outer edge in the main scanning direction to remove a second planar section of the raw sample, and successively irradiating the single focused ion beam in the main scanning direction inwards toward the center of the raw sample in a second sub-scanning direction that is opposite of the first sub-scanning direction to remove planar sections successive to the second planar section of the raw sample, wherein the second outer edge is opposite of the first outer edge, and the irradiating across the second outer edge occurs after completion of, removal of the planar sections successive to the first planar section of the raw sample.

2. The method according to claim 1, further including controlling a deflection of the single focused ion beam with a deflecting member of an ion beam forming apparatus to irradiate the single focused ion beam.

3. The method according to claim 1, further including setting the raw sample in a known positional relationship to the ion beam forming apparatus, and automatically forming the thin-piece sample from the raw sample by a control device.

4. A method of forming a thin-piece sample for use in a transmission electron microscope, comprising:

placing a sample block on a sample stage;

forming a protective coat layer on an upper surface of the sample block;

raster scanning a single focused ion beam from above an upper surface of the sample block starting from a point on a first outer edge of the upper surface across the first outer edge to a second point on the first outer edge in a main scanning direction, being a wall-width direction, to remove a first planar section of the sample block, and successively raster scanning the single focused ion beam in the main scanning direction inwards toward a center of the sample block in a first sub-scanning direction, being a wall-thickness direction, to remove planar sections successive to the first planar section of the sample block; and raster scanning the single focused ion beam from above the upper surface of the sample block starting from a point on a second outer edge of the upper surface across the second outer edge to a second point on the second outer edge in the main scanning direction to remove a second planar section of the sample block, and successively raster scanning the single focused ion beam in the main scanning direction inwards toward the center of the sample block in a second sub-scanning direction that is opposite of the first sub-scanning direction to remove planar sections successive to the second planar section of the sample block, wherein the second outer edge is opposite of the first outer edge, and the raster scanning across the second outer edge occurs after completion of removal of the planar sections successive to the first planar section of the sample block.

5. The method according to claim 4, further including controlling a deflection of the single focused ion beam with a deflecting member of an ion beam forming apparatus to irradiate the single focused ion beam.

6. The method according to claim further including setting the sample block in a known positional relationship to the ion beam forming apparatus, and automatically forming the thin-piece sample from the sample block by a control device.

* * * * *